(12) United States Patent
Klauck

(10) Patent No.: US 12,233,040 B2
(45) Date of Patent: Feb. 25, 2025

(54) COMBUSTIBLE AND EDIBLE COMPOSITION OF MEDIUM-CHAIN TRIGLYCERIDES AND SILICIC ACID

(71) Applicant: Institut Dr. Rilling Healthcare GmbH, Pliezhausen (DE)

(72) Inventor: Wolfgang Klauck, Meerbusch (DE)

(73) Assignee: Institut Dr. Rilling Healthcare GmbH, Pliezhausen (DE)

( * ) Notice: Subject to any disclaimer, the term of this patent is extended or adjusted under 35 U.S.C. 154(b) by 877 days.

(21) Appl. No.: 17/276,251

(22) PCT Filed: Sep. 10, 2019

(86) PCT No.: PCT/EP2019/074061
§ 371 (c)(1),
(2) Date: Mar. 15, 2021

(87) PCT Pub. No.: WO2020/053189
PCT Pub. Date: Mar. 19, 2020

(65) Prior Publication Data
US 2022/0031649 A1  Feb. 3, 2022

(30) Foreign Application Priority Data
Sep. 14, 2018  (DE) .......................... 102018122533.4

(51) Int. Cl.
| | | |
|---|---|---|
| A61K 31/23 | (2006.01) | |
| A23L 33/12 | (2016.01) | |
| A23L 33/16 | (2016.01) | |
| A23L 33/24 | (2016.01) | |
| A23P 20/10 | (2016.01) | |
| A61K 47/02 | (2006.01) | |
| A61K 47/38 | (2006.01) | |
| C10L 5/44 | (2006.01) | |

(52) U.S. Cl.
CPC .............. *A61K 31/23* (2013.01); *A23L 33/12* (2016.08); *A23L 33/16* (2016.08); *A23L 33/24* (2016.08); *A23P 20/10* (2016.08); *A61K 47/02* (2013.01); *A61K 47/38* (2013.01); *C10L 5/44* (2013.01); *A23V 2002/00* (2013.01); *C10L 2200/0484* (2013.01)

(58) Field of Classification Search
None
See application file for complete search history.

(56) References Cited

U.S. PATENT DOCUMENTS

| | | | |
|---|---|---|---|
| 4,263,313 A | 4/1981 | Eckert et al. | |
| 6,228,377 B1 * | 5/2001 | Sebillotte-Arnaud | ....................... A61K 8/064 |
| | | | 514/846 |
| 2003/0054043 A1 | 3/2003 | Kuentz | |
| 2003/0130346 A1 | 7/2003 | Kuzela et al. | |
| 2005/0233044 A1 | 10/2005 | Rader et al. | |

FOREIGN PATENT DOCUMENTS

| | | | |
|---|---|---|---|
| DE | 2707878 A1 | 8/1978 | |
| DE | 102007055341 A1 * | 5/2009 | ............. A61K 31/44 |
| WO | 03/63877 A1 | 8/2003 | |
| WO | 2004/004682 A2 | 1/2004 | |

OTHER PUBLICATIONS

Evonik, Aerosil R972 Product Information Sheet, accessed on Mar. 28, 2024. (Year: 2024).*
Cabot, Cab-O-Sil TS-610 Product Information Sheet, accessed on Mar. 28, 2024 (Year: 2024).*
Evonik, Hydrophilic Fumed Silicas, accessed on Mar. 28, 2024 (Year: 2024).*
"Measurement of the Dynamic Viscosity of Newtonian Fluids with Rotational Viscometers, Source of Errors and Corrections Concerning Cylinder Rotation Viscometers," German Standards DIN 53018, Part 2, Mar. 1976, pp. 1-10.
"Determination of the specific surface area of solids by gas adsorption—BET method," Standard DIN ISO 9277, Jan. 2014, pp. 1-28.
"General methods of test for pigments and extenders," European Standard DIN EN ISO 787-2, Mar. 1995, pp. 6.
"Measurement of the Dynamic Viscosity of Newtonian Fluids with Rotational Viscometers, Principles," German Standards DIN 53018, Part 1, Mar. 1976, pp. 1-6.
"Petroleum products and lubricant," European Standard EN 22719, Oct. 1993, pp. 15.
International Preliminary Report on Patentability received for PCT Patent Application No. PCT/EP2019/074061, mailed on Jan. 28, 2021, 23 pages (6 pages of English Translation and 17 pages of Original Document).
International Search Report and Written Opinion received for PCT Patent Application No. PCT/EP2019/074061, mailed on Nov. 5, 2019, 15 pages (3 pages of English Translation and 12 pages of Original Document).
Wiberg, H., "Oxygen Acids of Silicon. Silicates. Silicones," Textbook of Inorganic Chemistry, 101st edition, (1995), pp. 918-930.
Annon: "MCT Oil and MCT Powder: Helps to increase ketone production", Metagenics Inc., 2017, 2 pages.
Anonymous: "Diet Fuel Dietary Supplement", Database GNPD [Online] Mintel; Mar. 14, 2007, XP055635044, retrieved from www.gnpd.com Database accession No. 673280, 2 pages.
Bach et al., "Medium-Chain Triglycerides: An Update", The American journal of clinical nutrition, vol. 36, Nov. 1, 1982, pp. 950-962.

* cited by examiner

Primary Examiner — Melissa S Mercier
(74) Attorney, Agent, or Firm — Norris McLaughlin, P.A.

(57) ABSTRACT

The present invention relates to a combustible and edible composition comprising medium-chain triacylglycerols and silica, wherein the composition is in one embodiment a solid shaped body. The invention further relates to the use of a composition or of a solid shaped body as an item of equipment for outdoor activities, camping, sports activities, and/or in a diet.

16 Claims, No Drawings

COMBUSTIBLE AND EDIBLE COMPOSITION OF MEDIUM-CHAIN TRIGLYCERIDES AND SILICIC ACID

CROSS-REFERENCE TO RELATED APPLICATIONS

This application is a national stage application (under 35 U.S.C. § 371) of PCT/EP2019/074061, filed Sep. 10, 2019, which claims benefit of German Application No. 102018122533.4, filed Sep. 14, 2018, both of which are incorporated herein by reference in their entirety.

The present invention relates to a combustible and edible composition comprising medium-chain triacylglycerols and silica, wherein the composition is in one embodiment a solid shaped body. The invention further relates to the use of a composition or of a solid shaped body as an item of equipment for outdoor activities, camping, and/or sports activities, and/or in a diet. The invention further relates to the use in the health sector, particularly in therapeutic nutrition for the dietary treatment of various diseases or for weight loss.

Medium-chain triacylglycerols or triglycerides are generally understood as meaning triacylglycerols that contain unsaturated fatty acids having a length of 6 to 12 carbon atoms. These triacylglycerols are found primarily in coconut oil, palm kernel oil, and butter. Pure medium-chain triacylglycerols of fatty acids are obtained by hydrolysis of coconut oil or palm kernel oil, fractionation of the medium-chain fatty acids, and subsequent esterification with glycerol. Pure medium-chain triacylglycerols are known under the general terms neutral fat, MCT oils or MCT fats (medium-chain triglycerides) and are used in cosmetic products and as foodstuffs. These oils are said to be beneficial in weight loss, to improve mental and physical performance, and to protect against various diseases.

Because of their structure, MCT oils have physiological properties different to those of conventional, long-chain fatty acids and can be absorbed more easily by the body. MCT oils do not need to be emulsified by bile acids in the intestine in order for them to be better metabolized. They also do not need to undergo cleavage by pancreatic lipase, an enzyme in the pancreas. MCT oils are transported directly into the blood to the liver without circumvention via the lymphatic system, where they are preferentially oxidized over conventional fats, with increased formation of ketone bodies, which are used as energy sources by the heart and by the brain in particular. For these reasons, MCT oils provide energy quickly and are known to be readily available and usable for people during physical exertion, for example in the form of beverages. MCT oils are also used in clinical nutrition for the dietary treatment of various diseases, for example malabsorption syndrome, lymphangiectasia, Whipple's disease, chylothorax, exocrine pancreatic insufficiency, or as part of a ketogenic diet. The ketogenic diet is a limited-carbohydrate, protein- and energy-balanced and therefore high-fat form of dietary nutrition in which the body obtains its energy needs only from fat and the glucose substitute formed therefrom in the body, the eponymous ketone bodies. A ketogenic diet is used as a treatment method especially in children with drug-resistant epilepsy, glucose transport disorders such as GLUT1 deficiency syndrome, and pyruvate dehydrogenase deficiency. More recent research findings also suggest that therapy in Alzheimer's disease is a possibility. In addition, MCT oils are also used for weight loss.

The MCT oils commonly available typically comprise as principle constituents approx. 50-65% of caprylic acid (C8) and approx. 30-45% of capric acid (O10). Caproic acid (C6), lauric acid (C12), and myristic acid (C14) are present in very small amounts in common oils. These MCT oils are known inter alia under the trade names Mygliol 812® from Sasol, Myritol 312® from Cognis, and Tegosoft® CT from Evonik.

At room temperature, MCT oils are liquid and non-flammable. MCT oils typically have a flash point in the range from 210° C. to 240° C. and an ignition temperature in the range from 410° C. to 440° C.

Silica is used as a food supplement and is said inter alia to strengthen the immune system, connective tissue, and blood vessels, have an anti-inflammatory and disinfectant action, and in particular to improve the structure of hair and nails.

More and more people are consuming foodstuffs or food supplements to which a beneficial effect on the body or on individual parts of the body has been ascribed. A diet often specifically tailored to one's own body and regular physical activity are viewed as elements of a healthy lifestyle to which more and more people aspire. Physical activity commonly includes not only sessions in the gym, jogging, swimming or weight training, but also various outdoor activities such as cycling, mountain biking, hiking, trekking, mountaineering, climbing, and skiing. Outdoor activities usually take up several hours or the whole day. These can also take the form of multi-day tours or trips. Such tours or trips are often combined with camping in tents or camper vans.

What all sports/outdoor activities have in common is that, after a while, initial signs of physical exhaustion and hunger appear. If active outdoors when the outside temperatures are low or even frosty, one will feel cold despite the physical exercise. Even on a simple camping trip that is not associated with an outdoor activity, a source of heat may be necessary to heat or cook food and—depending on the outside temperature—to provide warmth. In addition, there may also be a need or requirement for a source of light.

While it is on the one hand necessary to meet needs for food, warmth, and/or light, it is on the other hand undesirable to have to bring along heavy or bulky items of equipment during sports/outdoor activities or when camping. This applies both to day trips and to multi-day tours. Sometimes it is moreover not possible to bring along heavy or bulky items of equipment because the option or individual capacity to carry heavy loads is limited. For example, only equipment having limited weight and relatively small volume can be carried in a boat or canoe. In addition, items of equipment for outdoor activities or camping should be easy to use and designed for the requirements of outdoor use. For example, heat or light sources should not go out in the wind. In addition, combustible materials should generate as little soot or smoke as possible when burned, so that they can also be used in a confined space such as a tent.

Foodstuffs and also flammable materials for outdoor activities should as far as possible not be liquid. If liquids leak out, the surrounding objects get wet and in the worst case are damaged. Particularly when the outside temperature is low, it may not always be possible to dry damp objects. If liquids need to be brought along, they should be packed in such a way that they do not leak. However, tearproof and breakproof packaging is often associated with increased weight.

There is a need for items of equipment for sports/outdoor activities and/or camping that meet the requirements placed on them by a limited option or limited individual capacity to carry heavy loads. These requirements can be satisfied by light and small items of equipment. However, the requirements can also be met by an item of equipment that has different functions. A multifunctional item of equipment can even replace other equipment items and thus help reduce the weight of the load carried. In addition, there is a need for foodstuffs or combustible materials for sports/outdoor activities that are not liquid. There is also a need for foodstuffs that can be used in therapeutic nutrition for the dietary treatment of diseases or for weight loss and that patients and/or medical personnel find easy and pleasant to use because they are easy to dose and have a pleasant taste.

The object of the present invention is to provide a composition that can be used as a foodstuff and also as a combustible material. After it has been ignited, the composition should preferably burn in such a way that the flame cannot be extinguished simply by blowing on it, that is to say it is not extinguished even in strong winds. In addition, it is preferable that hardly any soot forms during combustion, in order that the composition can also be used as a light and heat source in confined spaces and in particular also inside a tent. The composition is at room temperature preferably a gel, a gel-like shaped body or a powder. It is additionally an object of the present invention to provide a composition that can be used in the health sector, especially in medical or clinical nutrition, for the dietary treatment of diseases and that is easy and pleasant to use for patients and/or medical staff, especially compared to conventional liquid products.

According to the invention this object is achieved by a composition comprising or consisting of
from 70% to 96% by weight of triacylglycerol of saturated fatty acids that comprise an alkyl chain of 6 to 12 carbon atoms,
from 3.0% to 30% by weight of silica, and
optionally from 0.1% to 5.0% by weight of at least one thickener,
optionally from 1.0% to 35% by weight of at least one additive other than thickeners,
in each case based on the total weight of the composition, and the ratio of triacylglycerol to silica is within a range from 1:0.04 to 1:0.20.

It has surprisingly been found that the addition of silica to medium-chain triacylglycerols has the result that medium-chain triacylglycerols can be ignited and after ignition burn completely. In addition, it was surprisingly found that the mixture according to the invention burns with a largely soot-free flame that cannot be extinguished by blowing on it, that is to say it is not extinguished even in strong winds. Since both silica and triacylglycerol are edible, the composition of the invention combines two properties, namely edibility and combustibility.

Another advantage of the present invention is that the composition can also be used as a substitute for a gas stove, since it not only provides light, but also enough heat for food or liquids to be heated. In addition, the composition can also be used as frying fat. It can for example be rubbed into a pan to grease it before frying food.

The non-liquid composition preferably comprises or consists of
from 84% to 96% by weight, preferably from 84% to 92% by weight, of triacylglycerol of saturated fatty acids that comprise an alkyl chain of 6 to 12 carbon atoms,
from 4.0% to 20% by weight, preferably from 4.0% to 15% by weight, of silica, and
optionally not more than 5.0% by weight, preferably 0.2% to 0.4% by weight, of at least one thickener,
optionally from 4.0% to 10% by weight of at least one additive other than thickeners,
in each case based on the total weight of the composition, and the ratio of triacylglycerol to silica is within a range from 1:0.04 to 1:0.20, preferably from 1:0.10 to 1:0.20.

In the context of the invention, a silica is understood as meaning the oligomeric and polymeric condensation products of monosilicic acid $Si(OH)_4$. Silica can be present both as amorphous silicic acid of non-uniform structure and as crystallized silica. In accordance with this invention, the term silica also additionally encompasses so-called precipitated silicas. Precipitated silicas are understood as meaning aqueous solutions of amorphous silica, so-called silica sols, and acidified, semisolid silica sols, so-called silica gels. Dried silica gels are for the purposes of the invention also to be regarded as silica (Hollemann, Wiberg, Lehrbuch der Anorganischen Chemie [Textbook of Inorganic Chemistry], 101st edition, 1995, p. 919 ff.). The term silica also encompasses fumed silicas. Fumed silica is an amorphous $SiO_2$ powder commonly obtained by flame hydrolysis of silanes or $SiCl_4$.

In a preferred embodiment, the composition comprises fumed silica, in another preferred embodiment the composition comprises precipitated silica. The composition preferably comprises fumed silica, preferably 4.0% to 30% by weight, more preferably 10% to 20% by weight, of fumed silica, in each case based on the total weight of the composition. The composition preferably comprises precipitated silica, preferably 10% to 15% by weight, more preferably 11% to 13% by weight, of precipitated silica, in each case based on the total weight of the composition.

The water content of the silica in accordance with DIN EN ISO 787-2 is preferably not more than 3.0% by weight of water, more preferably from 0.1% by weight to 0.5% by weight, even more preferably 0.1% by weight to 0.3% by weight, in each case based on the total weight of silica in the composition. The silica preferably has a BET surface area in accordance with DIN ISO 9277 from 150 $m^2/g$ to 250 $m^2/g$, in particular from 160 $m^2/g$ to 200 $m^2/g$.

Triacylglycerol of saturated fatty acids is in the context of the invention understood as meaning triacylglycerol of unsaturated fatty acids having a length of 6 to 12 carbon atoms. The triacylglycerol in the composition according to the invention is preferably a pure medium-chain triacylglycerol, in particular obtained by hydrolysis of coconut oil or palm kernel oil, fractionation of the medium-chain fatty acids, and subsequent esterification with glycerol. Pure medium-chain triacylglycerols are also referred to as neutral fat, MCT oil or MCT fats (medium-chain triglycerides).

The water content of the triacylglycerol is preferably not more than 0.08% by weight of water, more preferably not more than 0.07% by weight, even more preferably not more than 0.05% by weight, in each case based on the total amount of triacylglycerol in the composition. In a preferred embodiment, the triacylglycerol comprises not more than 0.05% by weight of water and the following fatty acids
from 50% to 63% by weight of caprylic acid (C8),
from 34% to 43% by weight of capric acid (C10),
from 0.5% to 2.0% by weight of lauric acid (C12),
from 0.5% to 1.0% by weight of caproic acid (C6), and
from 0.5% to 1.0% by weight of myristic acid (C14), in each case based on the total amount of fatty acids.

The composition optionally comprises a thickener. Particularly in the case of compositions that comprise a comparatively low concentration of precipitated or fumed silica, the addition of a thickener also makes it possible to obtain combustible compositions that would not be combustible without the addition of the thickener. Compositions having only a low concentration of silica preferably comprise:

up to 4.0% by weight of fumed silica and 0.1% to 5.0% by weight of at least one thickener, or up to 10% by weight of precipitated silica and 0.1% to 5.0% by weight of at least one thickener, in each case based on the total weight of the composition.

In a preferred embodiment the thickener is water. In another preferred embodiment, the thickener is at room temperature a solid, in particular a powder. The solid or the powder can preferably be dissolved in at least one solvent. Particular preference is given here to a 5% mixture of ethylcellulose in toluene and ethanol in a mixing ratio of 80:20. The thickener is preferably selected from the group consisting of cellulose derivatives, cellulose fibers, alginates, agar-agar, locust bean gum, guar gum, carrageenan, furcellaran, xanthan gum, pectin, methylcellulose, ethylcellulose, hydroxyethylcellulose, carboxymethylcelluloses, hydroxypropylmethylcellulose, hydroxypropylcellulose, ethylhydroxyethylcellulose, and microcrystalline cellulose and also mixtures thereof. Cellulose derivatives are chemical derivatives of cellulose obtained for example, by methylation, ethylation, hydroxypropylation, acetylation, and oxidation. The thickener is preferably ethylcellulose. Ethylcellulose is typically a white powder and is soluble in organic solvents. The composition according to the invention preferably comprises ethylcellulose having a degree of ethoxylation of at least 60%, more preferably at least 45%.

In another preferred embodiment, the composition does not contain a thickener. In compositions that do not contain a thickener, the ratio of MCT oil to $SiO_2$ is preferably 1:0.15 to 1:0.5. Compositions without a thickener preferably comprise 6-10% by weight of fumed silica or 12-15% by weight of precipitated silica, in each case based on the total weight of the composition. A preferred embodiment without a thickener comprises 80% to 85% by weight of MCT oil and 10% to 15% by weight of fumed silica, in each case based on the total weight of the composition.

The composition may optionally comprise a further additive that is not a thickener. A composition according to the invention preferably comprises from 4.0% to 6.0% by weight of at least one additive other than thickeners, based on the total weight of the composition. The additive is preferably selected from the group consisting of food supplements as defined in Annexes 1 and 2 to the Verordnung über Nahrungsergänzungsmittel [German Ordinance on Food Supplements] dated 24 May 2004, BGBl. I [German Federal Law Gazette part I] p. 1011, version of 17.01.2007, food additives as defined to Annex 1 to the Verordnung über die Zulassung von Zusatzstoffen zu Lebensmitteln zu technologischen Zwecken [German Ordinance on the Approval of Additives in Food for Technological Purposes] dated 29 Jan. 1998, BGBl. I [German Federal Law Gazette part I] p. 230, version of 05.07.2017, and flavorings as defined in the Aromenverordnung [German Ordinance on Flavorings] dated 2 May 2006 (BGBl. I [German Federal Law Gazette part I] p. 1127), version of 05.07.2017, and also mixtures of said substances.

Food supplements in the meaning of the German Ordinance on Food Supplements are vitamins and minerals, including trace elements. Preferred food supplements are vitamins and minerals, in particular selected from the group consisting of vitamin C, vitamin D3, vitamin K, calcium and magnesium salts, and mixtures thereof. A preferred vitamin is vitamin C selected from the group consisting of L-ascorbic acid, sodium L-ascorbate, calcium L-ascorbate, potassium L-ascorbate, and L-ascorbyl-6-palmitate and also mixtures thereof. Another preferred vitamin is vitamin D in the form of cholecalciferol or ergocalciferol. Another preferred vitamin is vitamin K, preferably as phytomenadione. In addition, preferred food supplements are calcium and magnesium salts preferably selected from the group consisting of calcium carbonate, calcium chloride, calcium salts of citric acid, calcium gluconate, calcium glycerophosphate, calcium lactate, calcium salts of orthophosphoric acid, calcium hydroxide, calcium oxide, magnesium acetate, magnesium carbonate, magnesium chloride, magnesium salts of citric acid, magnesium gluconate, magnesium glycerophosphate, magnesium salts of orthophosphoric acid, magnesium lactate, magnesium hydroxide, magnesium oxide, and magnesium sulfate and also mixtures thereof.

Food additives are compounds added to foods to achieve chemical, physical or even physiological effects. They are used to regulate or stabilize the structure, taste, odor, color, and chemical and microbiological shelf life of processed foods, that is to say their utility value and nutritional value, and to ensure problem-free production of the food. The Verordnung über die Zulassung von Zusatzstoffen zu Lebensmitteln zu technologischen Zwecken [German Ordinance on the Approval of Additives to Foods for Technological Purposes], Zusatzstoff-Zulassungsverordnung (ZZuIV) [German Additives Approval Ordinance] for short, regulates the approval, labeling, and maximum amounts of additives for foods. The composition preferably comprises as a food additive dyes, preservatives, sweeteners, and/or antioxidants.

The composition preferably comprises preservatives selected from the group consisting of sorbic acid, potassium sorbate, calcium sorbate, benzoic acid, sodium benzoate, potassium benzoate, calcium benzoate, ethyl 4-hydroxybenzoate, ethyl 4-hydroxybenzoate sodium, methyl 4-hydroxybenzoate, sulfur dioxide, sodium sulfite, sodium hydrogen sulfite, sodium disulfite, potassium disulfite, calcium disulfite, calcium hydrogen sulfite, potassium hydrogen sulfite, malic acid, fumaric acid, and lysozyme and also mixtures thereof.

The composition preferably comprises sweeteners selected from the group consisting of sorbitol, mannitol, acesulfame K, aspartame, cyclamate, isomalt, saccharin, sucralose, thaumatin, neohesperidin dihydrochalcone, steviol glycosides, neotame, maltitol, lactitol, xylitol, erythritol, and advantame and also mixtures thereof.

The composition preferably comprises antioxidants selected from the group consisting of ascorbic acid, sodium ascorbate, calcium ascorbate, ascorbyl palmitate, ascorbyl stearate, alpha-tocopherol, gamma-tocopherol, delta-tocopherol, propyl gallate, octyl gallate, dodecyl gallate, isoascorbic acid, sodium isoascorbate, tert-butylhydroquinone, citric acid, phosphate, phosphoric acid, succinic acid, and rosemary extract and also mixtures thereof.

Flavorings are products added to foods in order to impart to them a particular odor and/or taste or to alter their odor and/or taste. The composition preferably comprises flavorings selected from the group consisting of flavorings, natural flavorings, flavoring extracts, thermally obtained process flavorings, smoke flavorings, flavoring precursors, and other flavorings or mixtures thereof. The composition preferably comprises flavorings having a fruity flavor. These include preferably citrus fruit flavors selected from the group consisting of oranges, blood oranges, grapefruit, mandarins, lemons, and kumquats. Particular preference is given to orange and lemon flavors, particularly in the form of lemon oil or orange oil. Other preferred flavors are berry, blueberry, raspberry, strawberry, apple, pear, grape, and melon flavors. Additional preferred flavors are vanilla and chocolate flavors.

The composition according to the invention preferably comprises only constituents that are in each case approved
- as foods, as defined in the Lebensmittel and Futtermittelgesetzbuch [Food and Feed Code] (LFGB) and Regulation EC 178/2002 (General Food Law Regulation), or
- as food supplements, as defined in Annexes 1 and 2 to the Verordnung Ober Nahrungserganzungsmittel [German Ordinance on Food Supplements] dated 24 May 2004, BGBl. I [German Federal Law Gazette part I] p. 1011, version of 17.01.2007, or
- as food additives, as defined to Annex 1 to the Verordnung über die Zulassung von Zusatzstoffen zu Lebensmitteln zu technologischen Zwecken [German Ordinance on the Approval of Additives in Food for Technological Purposes] dated 29 Jan. 1998, BGBl. I [German Federal Law Gazette part I] p. 230, version of 05.07.2017, or
- as flavorings, as defined in the Aromenverordnung [German Ordinance on Flavorings] dated 2 May 2006 (BGBl. I [German Federal Law Gazette part I] p. 1127), version of 05.07.2017.

A preferred embodiment of the composition comprises or consists of
- from 85% to 90% by weight of triacylglycerol of saturated fatty acids that comprise an alkyl chain of 6 to 12 carbon atoms,
- from 4.0% to 15% by weight of silica, in particular fumed silica,
- optionally from 0.1% to 5.0% by weight of at least one thickener, in particular a mixture of 3% by weight of ethylcellulose with 0.2% by weight of water, and
- optionally 0.1% to 7.0% by weight of at least one additive other than thickeners, in each case based on the total weight of the composition.

The composition according to the invention is preferably combustible. A cubic 50 g mass consisting of the composition according to the invention preferably burns for at least 10 minutes. The composition according to the invention preferably has a flash point in accordance with EN 22719 of 210 to 240° C., more particularly the composition has a flash point of 220 to 230° C. and more particularly continues to burn independently after the ignition source has been removed. It is preferable that a composition burns independently and completely after the ignition source has been removed, i.e. until there is no more MCT oil remaining. The flash point of a substance is the lowest temperature at which an ignitable vapor-air mixture can form over a substance. Because of its combustibility, the composition can be used as a source of light and heat. The flash point of the composition according to the invention is in a temperature range that corresponds to that of a lighter flame, which means that the composition can be used as a light and heat source without special equipment. For example, it can be used instead of a gas stove to heat liquids and food when camping. The flame preferably needs no wind protection when burning the composition according to the invention outside enclosed spaces. In addition, the composition may also be used as fat for frying food, by rubbing a pan with the composition and then frying food in said pan.

The composition preferably has a dynamic viscosity at 21° C. in accordance with DIN 53018 of 50 000 to 400 000 mPa·s, in particular from 70 000 to 350 000 mPa s, measured with a Brookfield viscometer, spindle 5, at 0.5 revolutions per minute, or is solid at room temperature. A preferred embodiment has a viscosity of not more than 80 000 mPa·s. Another preferred embodiment has a viscosity of not more than 360 000 mPa·s. The composition according to the invention is preferably solid at room temperature. Solid compositions are for the purposes of this invention considered to be compositions that, after the end of the production process, no longer change their shape at room temperature through the action of gravity alone; this property should be tested on a cube having edges of 1 cm in length. A cube of this type made from a solid composition according to the invention does not flow apart, does not collapse or does not form any partial convexities or bulges visible to the eye. A solid composition can preferably also be a solid gel. The viscosity of solid gels is for the purposes of this invention preferably not measurable at room temperature; instead, shaped bodies formed from solid gels according to the invention break when mechanical force is exerted. In a further preferred embodiment, the composition according to the invention is a powder.

A further preferred embodiment of the composition relates to a solid shaped body comprising the above-described composition according to the invention, wherein the shaped body is preferably partially or completely covered with a coating. The coating preferably comprises or consists of alkyl cellulose, the alkyl cellulose preferably being an ethylcellulose. The coating prevents the shaped body from feeling slippery, sticky or greasy, but without adversely affecting the combustibility of the shaped body. In addition, the coating ensures that a packaging can be easily removed from the shaped body and does not stick to the shaped body when the packaging is opened. In addition, the coating prevents liquids, in particular water, from being able to penetrate the shaped body.

Some constituents of the composition have more than one function. For example, thickeners such as ethylcellulose can also serve as a coating for the solid shaped body. Other constituents can be regarded as a food supplement and/or food additive and/or flavoring.

The invention relates also to the use of a composition according to the invention or of a shaped body according to the invention as an item of equipment for outdoor activities, camping, and/or sports activities, and/or in a diet. Examples of sports activities and/or outdoor activities include jogging, swimming, cycling, mountain biking, hiking, trekking, canoeing, rowing, rafting, skiing, tennis, soccer, handball, volleyball, basketball, mountaineering, climbing and strength training. The invention preferably also relates to use in the health sector. The use in the health sector preferably relates to therapeutic nutrition for the dietary treatment of various diseases or for weight loss, in particular therapeutic nutrition in malabsorption syndrome, lymphangiectasia, Whipple's disease, chylothorax, exocrine pancreatic insufficiency or as part of a ketogenic diet, in particular ketogenic diet as a treatment method especially in children with drug-resistant epilepsy, glucose transport disorders such as GLUT1 deficiency syndrome, and pyruvate dehydrogenase deficiency and also in Alzheimer's disease.

One embodiment of the equipment item comprises a coated shaped body, another embodiment comprises an uncoated shaped body. The item of equipment is for outdoor activities preferably packed inside a packaging, the packaging preferably consisting of a combustible material. This allows the packaging to be burned together with the composition. In another preferred embodiment, the packaging of the item of equipment is compostable or otherwise biodegradable.

EXAMPLES

The present invention is further elucidated by the examples that follow, but without being restricted thereto.

Glossary of Ingredients

Triacylglyceride (MCT Oil):
  Food quality
  Density at 20° C.=0.95 g/cm$^3$
  Water content <0.05%
  Fatty acid composition: C6: max 1%; C8: 50-65%; O10: 34-45%; C12: max. 2%; C14: max. 1%
SiO$_2$ Fumed
  Food quality
  BET surface area: 200 m$^2$/g
  pH-value 5% in water: 4.0
  Tamped density: <60 WI
SiO$_2$ Precipitated
  Food quality
  BET surface area: 160 m$^2$/g
  pH-value 5% in water: 7.0
  SiO$_2$ content: >96%
  Tamped density: 80 WI
  Soluble salts: <2.6%
Ethylcellulose
  Food quality
  Degree of ethoxylation: 49%
  Viscosity (5% in toluene/ethanol 80/20): 190 mPa·s
  Weight of residue after ashing: <0.4%

The ingredients were mixed with one another in accordance with Table 1. Weights are in percent by weight based on the sum of the weight of all constituents of the composition.

Before mixing the ingredients, the fumed silica and the precipitated silica were preheated for 120 min at 130° C. in order to dry the surfaces.

Except in Examples 2 and 9, SiO$_2$ was homogenized with MCT oil at room temperature. In contrast to the other examples, Examples 2 and 9 comprise ethylcellulose. These compositions were produced by dissolving the ethylcellulose in MCT oil at 150° C.-180° C., followed by incorporation of SiO$_2$ and then cooling to room temperature.

The viscosity of the gels of Examples 1 to 4 and 9 was measured at 21° C. with a Brookfield viscometer, spindle 5 (0.5 revolutions/min).

The gel from Example 3 had a viscosity of 350 000 mPa·s and the gel from Example 4 had a viscosity of 70 000 mPa·s.

In the case of the shaped bodies made of solid gel in Examples 1, 2 and 9, it was not possible to measure the viscosity; when subjected to mechanical action, the shaped bodies made of solid gel broke and fragmented into several pieces.

In order to assess the fire behavior of the compositions from Examples 1 to 6 and 9, the compositions were spread across an area of 10 cm$^2$ with a height of approx. 0.2 to 0.5 cm. The flame from a lighter with a height of approx. 4 cm was then held against each sample for 4 seconds. In the case of the compositions that burned, various people each blew against the flame with their breath from a distance of approx. 40-50 cm during the burning, as if blowing out a candle. The fire behavior was categorized as follows:

TABLE 2

| | Fire behavior of the compositions |
|---|---|
| Does not burn | After the third attempt to ignite it according to the procedure described above, the sample does not burn |
| Burns weakly | The sample burns only slowly and the flame is extinguished by just a slight draft |
| Burns well | The sample is easy to ignite at the first attempt and continues to burn independently after the ignition source has been removed and burns completely, this being with a flame that is intense and impossible to extinguish by blowing on it |

The burning compositions continued to burn independently after the ignition source had been removed. The compositions described as "burning well" burned evenly over the entire surface with a yellowish flame from 4 to 8 cm in height until the point at which there was no longer any MCT oil remaining, i.e. they burned completely. The flame could not be extinguished by blowing on it, but only by placing a metal or ceramic lid on the burning mass so as to cut off the oxygen supply.

The compositions in Examples 2 (inventive) and 9 (comparative) differ essentially in that the composition in Example 9 does not contain any silica. The experimental

TABLE 1

| | Compositions | | | | | | | | |
|---|---|---|---|---|---|---|---|---|---|
| | Inventive | | | | | | Comparative | | |
| % by weight | 1 | 2 | 3 | 4 | 5 | 6 | 7 | 8 | 9 |
| MCT oil | 85.0 | 91.0 | 95.8 | 89.6 | 70.0 | 70.0 | 96.0 | 90.0 | 95.9 |
| SiO$_2$ fumed | 15.0 | 4.0 | 4.0 | — | 30.0 | — | 4.0 | — | — |
| SiO$_2$ precipitated | — | — | — | 10.0 | — | 30.0 | — | 10.0 | — |
| Ethylcellulose | — | 5.0 | — | — | — | — | — | — | 5.0 |
| Distilled water | — | — | 0.2 | 0.4 | — | — | — | — | — |
| Ratio of MCT oil to SiO$_2$ | 1:0.18 | 1:0.04 | 1:0.04 | 1:0.11 | 1:0.4 | 1:0.4 | 1:0.04 | 1:0.11 | 1:0.05 |
| Structure at 21° C. | shaped body made of solid gel | shaped body made of solid gel | gel | gel | powder | powder | liquid | liquid | shaped body made of solid gel |
| Fire behavior | burns well | burns well | burns well | burns well | burns weakly | burns weakly | does not burn | does not burn | does not burn | data show that the composition in Comparative Example 9 does not burn without silica, whereas the inventive composition in Example 2 comprising fumed silica burns well. Moreover, the liquid compositions do not burn.

The comparison of the inventive Example 3 with Comparative Example 7 shows that the combination of a comparatively low concentration of silica and a thickener also makes it possible to obtain combustible compositions that would not be combustible without addition of the thickener.

The invention claimed is:

1. A composition comprising
   a) from 70% to 96% by weight of triacylglycerol of saturated fatty acids comprising an alkyl chain of 6 to 12 carbon atoms,
   b) from 3.0% to 30% by weight of silica, and
   c) optionally from 0.1% to 5.0% by weight of at least one thickener comprising at least one cellulose derivative and/or water,
   d) optionally from 1.0% to 35% by weight of at least one additive other than thickeners,
   in each case based on the total weight of the composition, wherein the ratio of triacylglycerol a) to silica b) is within a range from 1:0.04 to 1:0.4,
   wherein
   the silica is fumed silica or precipitated silica, wherein when the silica is or comprises fumed silica and the composition comprises up to 4.0% by weight thereof, the composition comprises 0.1% to 5.0% by weight of at least one thickener and
   when the silica is or comprises precipitated silica and the composition comprises up to 10% by weight thereof, the composition comprises 0.1% to 5.0% by weight of at least one thickener,
   wherein the composition has a dynamic viscosity at 21° C. in accordance with DIN 53018 of 50 000 to 400 000 mPa·s, measured with a Brookfield viscometer, spindle 5, at 0.5 revolutions per minute, or is solid at room temperature, and a flash point in accordance with EN 22719 of 210° C. to 240° C.

2. The composition as claimed in claim 1, wherein the thickener is a solid at room temperature.

3. The composition as claimed in claim 1, wherein the thickener comprises further thickeners selected from the group consisting of cellulose fibers, alginates, agar-agar, locust bean gum, guar gum, carrageenan, furcellaran, xanthan gum, pectin, methylcellulose, ethylcellulose, hydroxyethylcellulose, carboxymethylcellulose, hydroxypropylmethylcellulose, hydroxypropylcellulose, ethylhydroxyethylcellulose, microcrystalline cellulose, and mixtures thereof.

4. The composition as claimed in claim 1, wherein the composition comprises 4.0% to 30% by weight of fumed silica.

5. The composition as claimed in claim 1, wherein the composition comprises 10% to 15% by weight of precipitated silica.

6. The composition as claimed in claim 1, wherein the silica has a BET surface area in accordance with DIN ISO 9277 from 150 m²/g to 250 m²/g.

7. The composition as claimed in claim 1, wherein the water content of the silica in accordance with DIN EN ISO 787-2 is not more than 3.0% by weight of water, in each case based on the total weight of silica in the composition.

8. The composition as claimed in claim 1, wherein the composition comprises from 4.0% to 10% by weight of at least one further additive.

9. The composition as claimed in claim 1, wherein the additive is selected from the group consisting of food supplements, food additives, flavorings, and mixtures thereof.

10. The composition as claimed in claim 1, wherein the composition consists of constituents that are in each case a food, a food supplement, a food additive, or a flavoring.

11. The composition as claimed in claim 1, wherein the composition has a flash point in accordance with EN 22719 of 220 to 230° C.

12. The composition as claimed in claim 1, wherein the composition has a dynamic viscosity at 21° C. in accordance with DIN 53018 of 70 000 to 350 000 mPa·s, measured with a Brookfield viscometer, spindle 5, at 0.5 revolutions per minute.

13. The composition as claimed in claim 1, wherein the composition comprises
   a) from 85% to 90% by weight of triacylglycerol of saturated fatty acids comprising an alkyl chain of 6 to 12 carbon atoms,
   b) from 4.0% to 15% by weight of silica,
   c) optionally from 0.1% to 5.0% by weight of at least one thickener, and
   d) optionally 0.1% to 7.0% by weight of at least one additive other than thickeners, in each case based on the total weight of the composition.

14. A shaped body comprising the composition as claimed in claim 1, wherein the shaped body is in partially or completely covered with a coating.

15. A method comprising providing the composition as claimed in claim 1 and incorporating the composition in a piece of equipment for outdoor activities, camping, or sports activities, or in a diet.

16. A composition comprising:
   a) from 70% to 96% by weight, based on a total weight of the composition, of triacylglycerol of saturated fatty acids comprising an alkyl chain of 6 to 12 carbon atoms;
   b) from 3.0% to 30% by weight, based on the total weight of the composition, of silica; and
   c) optionally from 0.1% to 5.0% by weight, based on the total weight of the composition, of at least one thickener comprising at least one cellulose derivative and/or water;
   d) optionally from 1.0% to 27% by weight, based on the total weight of the composition, of at least one additive other than thickeners;
   wherein the ratio of triacylglycerol a) to silica b) is within a range from 1:0.04 to 1:0.4;
   wherein the silica is fumed silica or precipitated silica;
   wherein when the silica is or comprises fumed silica and the composition comprises up to 4.0% by weight thereof, the composition comprises 0.1% to 5.0% by weight of at least one thickener;
   wherein when the silica is or comprises precipitated silica and the composition comprises up to 10% by weight thereof, the composition comprises 0.1% to 5.0% by weight of at least one thickener; and
   wherein the composition has a dynamic viscosity at 21° C. in accordance with DIN 53018 of 50 000 to 400 000 mPa·s, measured with a Brookfield viscometer, spindle 5, at 0.5 revolutions per minute, or is solid at room temperature, and has a flash point in accordance with EN 22719 of 210° C. to 240° C.

* * * * *